(12) United States Patent
Schnitzler et al.

(10) Patent No.: US 8,907,238 B2
(45) Date of Patent: Dec. 9, 2014

(54) PUSH BUTTON, METHOD FOR THE PRODUCTION THEREOF, AND MEDICAL MANIPULATING PART

(75) Inventors: Uwe Schnitzler, Tübingen (DE); Martin Hagg, Wannweil (DE); Jürgen Beller, Gomaringen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 191 days.

(21) Appl. No.: 13/256,188

(22) PCT Filed: Mar. 4, 2010

(86) PCT No.: PCT/EP2010/001365
§ 371 (c)(1),
(2), (4) Date: Sep. 12, 2011

(87) PCT Pub. No.: WO2010/102754
PCT Pub. Date: Sep. 16, 2010

(65) Prior Publication Data
US 2012/0000756 A1 Jan. 5, 2012

(30) Foreign Application Priority Data

Mar. 12, 2009 (DE) .......................... 10 2009 012 911
May 26, 2009 (DE) .......................... 10 2009 022 687

(51) Int. Cl.
| | |
|---|---|
| *H01H 13/06* | (2006.01) |
| *H01H 13/48* | (2006.01) |
| *A61B 18/00* | (2006.01) |
| *H01H 1/58* | (2006.01) |
| *A61B 17/00* | (2006.01) |
| *H01H 9/04* | (2006.01) |

(52) U.S. Cl.
CPC ...... *H01H 13/06* (2013.01); *A61B 2018/00916* (2013.01); *H01H 2001/5888* (2013.01); *H01H 2300/014* (2013.01); *A61B 2017/00212* (2013.01); *H01H 13/48* (2013.01); *H01H 9/04* (2013.01)
USPC ...................................................... 200/302.2

(58) Field of Classification Search
CPC ............ H01H 13/48; H01H 2227/026; H01H 2215/036; H01H 2223/002
USPC ................................................. 200/406, 302.2
See application file for complete search history.

(56) References Cited

U.S. PATENT DOCUMENTS 4,121,070 A * 10/1978 Silbernagel ................... 200/535
5,294,241 A * 3/1994 Taylor et al. ................. 65/59.31
(Continued)

FOREIGN PATENT DOCUMENTS

CN   1445627 A   10/2003
CN   1624842 A   6/2005
(Continued)

OTHER PUBLICATIONS

Written Opinion from PCT/EP2010/001365.

*Primary Examiner* — Renee S Luebke
*Assistant Examiner* — Ahmed Saeed
(74) *Attorney, Agent, or Firm* — Dickstein Shapiro LLP

(57) ABSTRACT

A push button of a medical manipulating part comprising: a first, pot-shaped, shell-shaped or box-shaped housing piece, at least some sections of which contain conductive material, with an integrally molded switching spring and a continuous wall, a second housing piece, the shape of which mates with the wall of the first housing piece and is inserted therein in a hermetically sealed manner such that a hollow space is formed between the first and second housing pieces underneath the switching spring and at least one mating contact for the switching spring, said mating contact being hermetically sealed and electrically isolated relative to the first housing piece, being led through the second housing piece and extending into the hollow space underneath the switching spring.

17 Claims, 1 Drawing Sheet

(56) References Cited

U.S. PATENT DOCUMENTS

| | | | |
|---|---|---|---|
| 5,807,122 A * | 9/1998 | Heeb et al. | 439/83 |
| 5,828,016 A * | 10/1998 | Grannan et al. | 200/16 R |
| 6,982,394 B2 * | 1/2006 | Ide et al. | 200/516 |
| 2003/0174590 A1 * | 9/2003 | Arikawa et al. | 368/319 |
| 2007/0102275 A1 | 5/2007 | Genz et al. | |

FOREIGN PATENT DOCUMENTS

| | | |
|---|---|---|
| DE | 37 13 318 A1 | 11/1988 |
| EP | 0 323 917 A2 | 7/1989 |
| GB | 1195702 A | 6/1970 |
| GB | 1 441 008 A | 6/1976 |
| GB | 2 213 647 A | 8/1989 |

\* cited by examiner

PUSH BUTTON, METHOD FOR THE PRODUCTION THEREOF, AND MEDICAL MANIPULATING PART

FIELD OF THE INVENTION

Embodiments of the invention relate to a push button to be used as part of a medical manipulating part, such as a medical instrument or a handle thereof, and to a method for the production of a push button of this kind and a medical manipulating part.

BACKGROUND

With the increasing use of HF surgery, and electrically driven or actuated diagnostic and therapeutic instruments, there has been a great expansion in the use of hand-held medical instruments or devices for which the handling includes the initiation of switching functions. Instruments and devices of this kind, or the associated manipulating parts, are used with electric push buttons.

There is the problem that the penetration of liquids, due to the use, cleaning, disinfection and sterilization of the products, can cause the push buttons to become damaged because the penetration of moisture causes the push button/contact to fail; as such, the function of the product is no longer guaranteed.

These types of manipulating parts are sealed at interfaces such as cable outlets, contact insertion area, push button area (via sealing rings, films, bonding, etc) such that the penetration of liquids is avoided to protect the button elements and their function. In addition, the push buttons have a splash-proof design; however, due to ambient conditions, this only provides conditional protection in the case of sterilization using moist heat.

The increased use of manipulating parts of the type described above has revealed certain problems. On the one hand, sealing all of the interfaces of the manipulating elements is a very complex constructional task and, on the other, there is a risk of leaks after repeated use. If moisture enters at one point, the other seals are functionless and moisture can penetrate the interior of the handles.

SUMMARY

An object of the embodiments of the invention is to provide an improved push button with respect to the above usage requirements, which should have a long service life and high reliability. In addition, a correspondingly improved manipulating part is provided.

The embodiments of the invention include a push button without additional sealing means (which have inherent latent defects) and comprising a minimum number of parts that, by their design, are hermetically sealed against each other. The embodiments also include designing a switching spring of the push button as an integral section of one of its housing pieces so that there is no need for a seal between the housing piece and the switching spring. The embodiments of the invention also include, in addition to this first housing piece, providing only one other, second housing piece to form the housing; said second housing piece containing at least one contact of the push button. Finally, the embodiments of the invention include embedding this contact, or these contacts, tightly in the second housing piece without separate sealing means.

Push buttons according to the disclosed embodiments of the invention can be used advantageously in medical manipulating parts, but also in other devices and especially those capable of being exposed to high thermal or climatic stresses.

Herein, "hermetically sealed" means a degree of moisture proof-ness and pressure tightness satisfying the usual requirements during the sterilization (in particular steam sterilization) of medical instruments and during their use, including thermal shock stresses and alternating stresses. Here, there is as little requirement for high-vacuum tightness as there is for tightness at extremely low temperatures.

In one embodiment of the invention, the second housing piece, at least in sections, is made of glass and the mating contact is melt-sealed into the section(s). The melt-sealing of a metallic part into glass is a technique known for decades from lighting technology for achieving hermetic seals, which have a long and reliable service in a simple and inexpensive way.

In a further embodiment, the first housing piece comprises resilient metal, in particular high-grade steel, titanium or a titanium alloy, and is embodied as a deep-drawn part. This enables the integral embodiment of the switching spring with the first housing piece to be implemented easily together with permanent corrosion resistance and tightness of the push button even under the demanding conditions of medical sterilization procedures.

A combination of embodiments offers an advantageous design in which the second housing piece is entirely made of glass and its circumference in contact with the wall of the first housing piece forms a physicochemical glass-metal bond with that wall. This makes sensible use of knowledge and technologies available from glass and lighting technology.

The same applies to a modified embodiment in which the second housing piece is made up of a metal ring and a glass metal ring, wherein the circumference of the glass metal ring forms a physicochemical glass-metal bond with an internal circumferential wall of the metal ring. The hermetically sealed bond to be achieved between the outer wall of said metal ring and the first housing piece can be created by e.g., a laser welding method. Welding methods of this type have been established in medical technology for a long time and can be used for the implementation of the embodiments of the invention.

While the aforementioned aspects of the invention to a certain extent produce a "high-end-embodiment", the principles can also be implemented with inexpensive plastic parts. In this case, the first housing piece is made, for example, of a conductively filled, high-temperature-resistant, plastic and/or a plastic with a conductive coating embodied as a blow-molded part. In addition, the second housing piece can also be made of plastic and be embodied as an injection-molded part. This to a certain extent enables the implementation of a "low-cost embodiment" of the invention for less demanding conditions. However, it is also possible to combine metal and/or glass housing pieces with plastic housing pieces.

In one embodiment of the push button with a single mating contact in the second housing piece, the first housing piece simultaneously serves as an intra-button supply line to an external connection contact; the push button can also be provided with two (or more) mating contacts, which are embedded in the second housing piece and can be electrically connected to each other by the switching spring integrally incorporated in the first housing piece. In this embodiment, a metallic section of the entirely metal, or metal-coated, first housing piece only bridges the distance between the mating contacts and is not connected to an external connection contact. An internal metallization of an otherwise non-conductive plastic part is also sufficient for the implementation of the push button function.

Depending upon the material embodiment of the proposed push button, the characteristic thermal treatment step for the hermetically sealed connection of the contact points of the individual push button components takes the form of either a glass to metal melt-sealing step or a sintering step at a temperature above 900° C., or also as a plastic hot-machining step. The latter variant is a step involving the shrinking of the first housing piece onto the second housing piece or a plastic welding step with machining temperatures and times adapted to the processing properties of the plastic (thermoplastic) actually used.

The manipulating part according to the embodiments of the invention includes connection contacts to the first housing piece or to each mating contact of the push button, which are soldered on or crimped on using conventional techniques. However, it is also possible to use other connecting methods to establish the connections, such as bonding with conductive adhesives, welding methods or even simple plug-and-socket connections. In particular, the mentioned connection contacts can also be elements of an SMD configuration, wherein the shape and size of the push button is then adapted to the specific configuration.

In an expedient embodiment, a functional component of the arrangement is placed in the interior of the push button and its connections are guided hermetically sealed through the second housing piece to connection contacts in the manipulating part.

BRIEF DESCRIPTION OF THE DRAWINGS

Advantages and features of the embodiments of the invention can also be derived from the following description of the exemplary embodiments with reference to the diagrams, in which.

DETAILED DESCRIPTION

Figure 1:
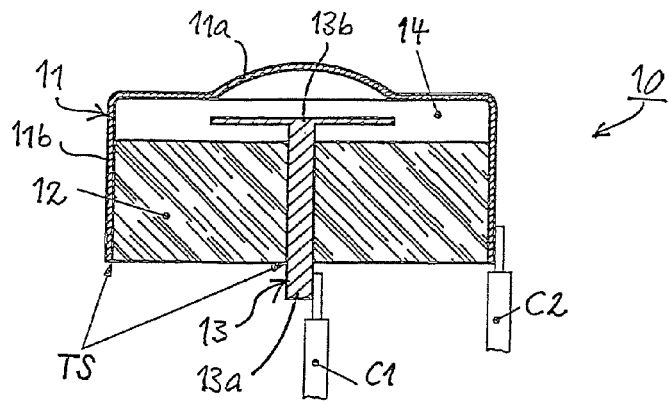
FIG. 1 is a schematic longitudinal section of a push button according to a first embodiment of the invention.

FIG. 1 shows a push button 10 connected to two external connection contacts C1, C2, which can be arranged on a printed circuit board (not shown) of a medical manipulating part (not shown). The push button 10 comprises a first housing piece 11 in the shape of a pot with a floor 11a beaten out in the shape of a spherical segment and a cylindrical wall 11b. The button 10 also comprises a ring-shaped second housing piece 12 made of glass and a contact piece (counter-contact) 13 placed centrically in the glass housing piece 12. The dimensions of the outer diameter of second housing piece are selected so that it fits in the cylindrical wall 11b of the first housing piece 11 with virtually no play and a pin portion 13a of the contact piece 13 fits in the cylindrical bushing in its center with virtually no play.

A thermal machining step (described below) creates, in each case, a hermetically tight seal on the contact surfaces of the above-mentioned parts. The contact piece 13 is placed in the push button 10 such that a circular contact plate 13b comes to lie on its inner end in a hollow space 14 between the internal face of the second housing piece 12 and the floor of the first housing piece 11, and, to be precise, with a spacing underneath the dent 11a in the floor of the first housing piece, such that, on elastic depression, the dent 11a touches the contact plate 13b. This establishes a (temporary) electrical connection between connection contact C1, to which the contact piece 13 is connected and connection contact C2 to which the conductive first housing piece 11 is connected. Hence, the dent 11a serves as a switching spring of the push button 10.

Figure 2:
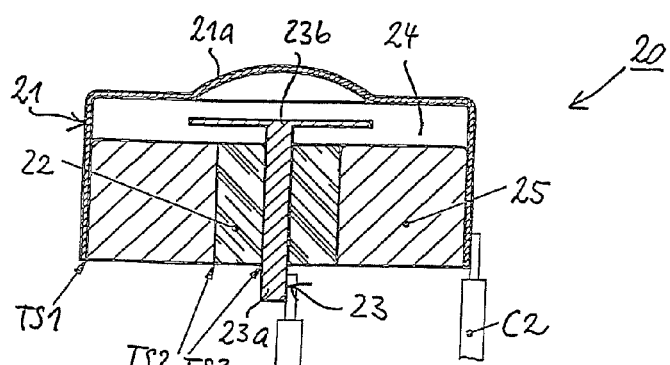
FIG. 2 is a schematic longitudinal section of a push button according to a second embodiment of the invention.

A modified push button 20 shown in FIG. 2 has substantially the same design as the push button 10 of FIG. 1; as such, parts designated with corresponding reference numbers will not be explained again. In deviation from the first embodiment, the FIG. 2 second housing piece comprises a glass inner ring 22, which holds and guides the contact piece 23 and a surrounding metal outer ring 25 extending as far as the inner wall of the first housing piece 21. Due to suitable dimensions and thermal treatment, this embodiment has three (up to 2.5 bar) hermetically tightly sealed areas TS1 (between the first housing piece 21 and the outer ring 25), TS2 (between the inner ring 22 and the outer ring 25) and TS3 (between the inner ring 22 and the contact piece 23).

Figure 3:
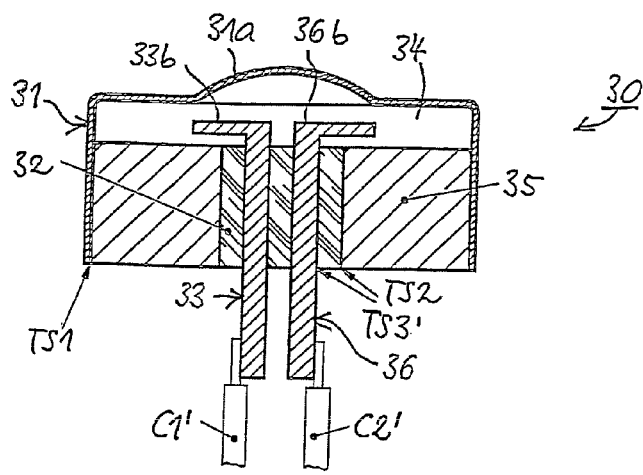
FIG. 3 is a schematic longitudinal section of a push button according to a third embodiment of the invention.

FIG. 3 shows another push button 30 which is a further modified embodiment of that shown in FIG. 2. As before, parts corresponding to the embodiment according to FIG. 2 are designated with the same reference numbers and are not explained again. The differences between the embodiments consist of a different arrangement of the external connection contacts C1', C2' and the provision of two contact pieces (mating contacts) 33, 36 matched thereto with, in each case, contact plates 33b, 36b lying underneath the switching spring 31a of the first housing piece 31 in the interior 34 of the push button. Depressing the switching spring 31a causes this to come into contact with two contact plates 33b, 36b simultaneously to thereby establish an electrical connection between the contact pieces 33, 36 and the external connection contacts C1', C2'.

Figure 4:
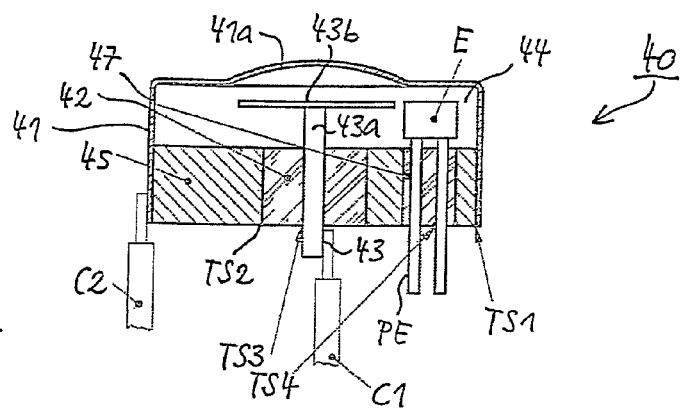
FIG. 4 is a schematic longitudinal section of a push button according to a fourth embodiment of the invention.

FIG. 4 shows a push button 40 of a further embodiment of the invention having an additional function; otherwise, the FIG. 4 embodiment is substantially the same as the push button 20 in FIG. 2. The interior 44 of the push button 40 is dimensioned slightly larger in that the thickness of the rings 41, 45 jointly forming the second housing piece is reduced compared to the second embodiment. This creates space for an electronic component E, which is accommodated in a protected manner in the interior, and the connecting pins PE which are guided in a hermetically sealed manner through the second housing piece. To this end, the metal outer ring 45 has a bore hole into which is inserted a glass stopper 47 into which the connecting pins PE of the components E have previously been melt-sealed.

The high-temperature steps required for the sealing are performed in a furnace at a temperature within the range between 900 and 1000° C. at which the glass used for the glass parts of the respective push buttons enters into a physico-chemical glass-metal bond with the respective adjacent metallic parts (comprising high-grade steel). To this end, the push button is placed on a graphite plate and introduced into the furnace where it is kept for a predefined time at the necessary temperature. The melt-sealing of the contact pieces or (in the case of the embodiment according FIG. 4) the contact pins of the component into the respective glass part can take place in advance in a separate thermal process. The finished push button can be connected to the external connection contacts using a conventional soldering or welding method; it is also possible to use a positive-locking connecting method, such as crimping or a plug-in connection if the connecting sections are suitably configured (for example, in the case of the embodiment according to FIG. 3).

The embodiments of the invention are not restricted to the examples described and aspects highlighted herein; it should be noted that a plurality of modifications are within the scope of professional practice.

The invention claimed is:

1. A push button for a medical manipulating part, said push button comprising:
   a first housing piece comprising a wall of conductive material and a floor beaten out in the shape of a spherical segment that functions as a switching spring, the floor beaten out when the push button is not being operated,
   a second housing piece, the shape of which mates with the wall of the first housing piece and is inserted therein in a hermetically sealed manner such that a hollow space is formed between the first and second housing pieces underneath the switching spring, and
   at least one mating contact for the switching spring contact for the switching spring, said mating contact being hermetically sealed and electrically isolated relative to the first housing piece, being led through the second housing piece and extending into the hollow space underneath the switching spring,
   wherein the second housing piece comprises a glass ring surrounding the at least one mating contact, the at least one mating contact being melt-sealed into the glass ring.

2. The push button of claim 1 comprising two mating contacts, with the ends of which that extend into the hollow space being positioned such that the switching spring touches both contacts on actuation.

3. The push button of claim 1, wherein the first housing piece is pot-shaped.

4. The push button of claim 1, wherein the first housing piece is shell-shaped.

5. The push button of claim 1, wherein the first housing piece is box-shaped.

6. The push button of claim 1, wherein the first housing piece is made of high-grade steel.

7. The push button of claim 1, wherein the first housing piece is made of titanium.

8. The push button of claim 1, wherein the first housing piece is made of a titanium alloy.

9. A medicinal manipulating part such as a particular instrument or handle, comprising a push button according to claim 1.

10. The manipulating part of claim 9, wherein the connection contacts are soldered or crimped onto the first housing piece of the push button.

11. The manipulating part of claim 9, wherein the connection contacts are soldered or crimped onto each mating contact of the push button.

12. The manipulating part of claim 9, wherein the connection contacts elements of an SMD configuration and the shape and size of the push button are adapted thereto.

13. The manipulating part of claim 9, wherein a functional component of the arrangement is placed in the interior of the push button and the connections of said functional component are guided in a hermetically sealed way through the second housing piece to connection contacts in the manipulating part.

14. The manipulating part of claim 1, wherein the second housing piece further comprises a metal ring surrounding an inner glass ring, the mating contact being melt-sealed into the glass ring.

15. The manipulating part of claim 1, wherein an outer circumference of the second housing piece contacts the wall of the first housing piece and forms a physicochemical glass-metal bond therewith.

16. The manipulating part of claim 1, wherein the first housing piece comprises a resilient metal.

17. The manipulating part of claim 16, wherein the first housing piece is a deep-drawn part.

* * * * *